United States Patent [19]
Daftary et al.

[11] Patent Number: 5,145,372
[45] Date of Patent: Sep. 8, 1992

[54] ANATOMICAL RESTORATION DENTAL IMPLANT SYSTEM WITH REINFORCED HEALING CAP AND ABUTMENT

[75] Inventors: Fereidoun Daftary, 50 N. La Cienega Blvd., No. 206, Beverly Hills, Calif. 90211; Jack D. Preston, 4936½ McConnell Ave., Los Angeles, Calif. 90066.

[21] Appl. No.: 782,091

[22] Filed: Oct. 24, 1991

Related U.S. Application Data

[63] Continuation-in-part of Ser. No. 424,901, Oct. 20, 1989, Pat. No. 5,073,111.

[51] Int. Cl.$^5$ .............................................. A61C 8/00
[52] U.S. Cl. .................................... 433/173; 433/174
[58] Field of Search ................ 433/173, 174, 175, 176

[56] References Cited

U.S. PATENT DOCUMENTS

| | | | |
|---|---|---|---|
| 4,758,160 | 7/1988 | Ismail | 433/173 |
| 4,780,080 | 10/1988 | Haris | 433/173 |
| 4,856,994 | 8/1989 | Lazzara et al. | 433/173 |
| 5,033,962 | 7/1991 | Scatena | 433/169 |

FOREIGN PATENT DOCUMENTS

| | | | |
|---|---|---|---|
| 3110693 | 9/1982 | Fed. Rep. of Germany | 433/174 |
| 3300764 | 7/1984 | Fed. Rep. of Germany | 433/173 |

*Primary Examiner*—Cary E. O'Connor
*Attorney, Agent, or Firm*—Thomas I. Rozsa

[57] ABSTRACT

A system and method is provided for implanting tooth analogues in the jawbone resulting in aesthetically and functionally desirable gingival tissue contours after restoration. The system permits modification and adaptation of the tooth analogue to meet intraoral demands in a manner similar to that used in the preparation and restoration of natural teeth. The system comprises a standard fixture and cover screw passed through opened gingival tissue and implanted in the jawbone. After the osseointegration of the fixture, the gingiva is reopened and the cover screw is removed, and a healing cap having a predetermined contour is attached to the fixture. The reopened gingiva re-heals in a shape determined by the contour of the healing cap. The healing cap may have two separable reinforced portions so that one lower portion around which gingiva tissue regrows may remain in the patient while only the other upper portion is removed and replaced by a reinforced abutment having an emergence profile matching that of the reinforced healing cap. An immediate snug fit between the gingival tissues and the reinforced abutment is thereby provided at the time of connection of the reinforced abutment to the fixture, and a crown can be removably attached to the reinforced abutment by a screw extending through the side of the crown into the reinforced abutment.

20 Claims, 5 Drawing Sheets

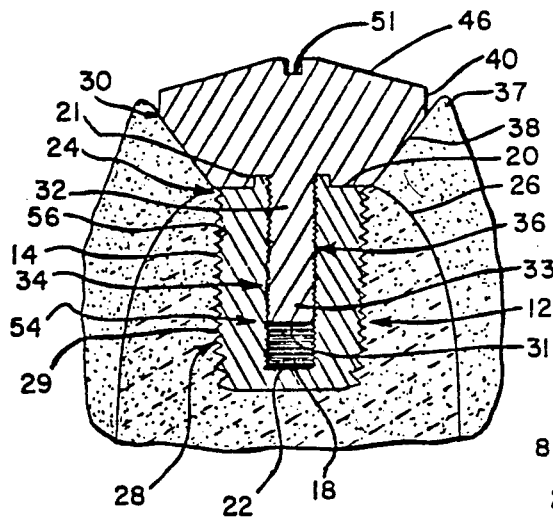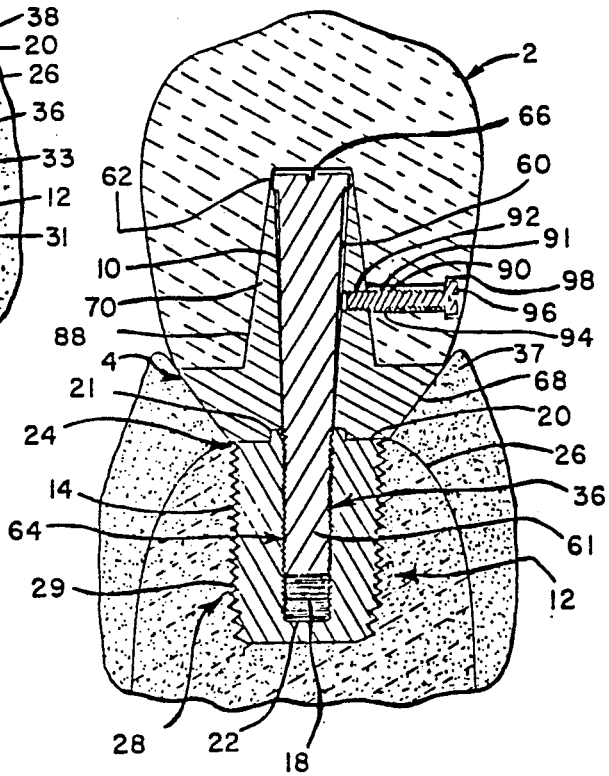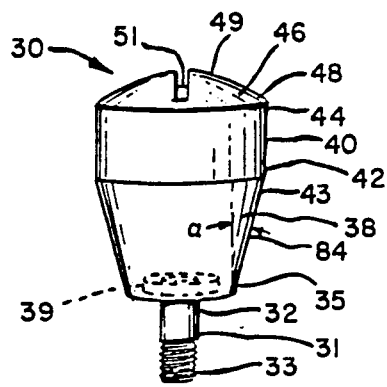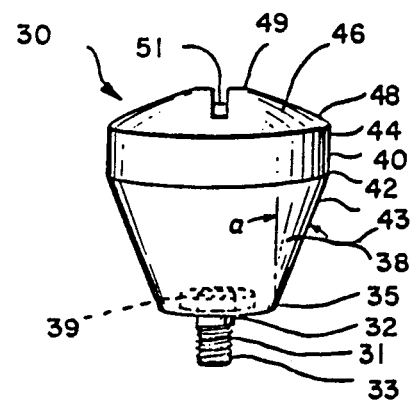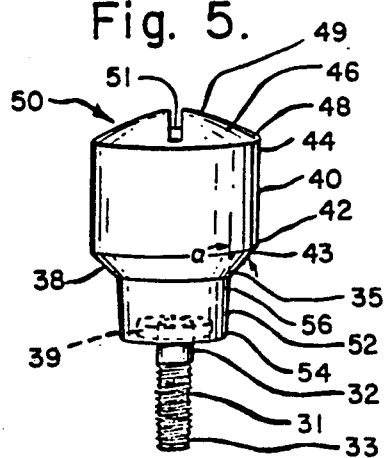

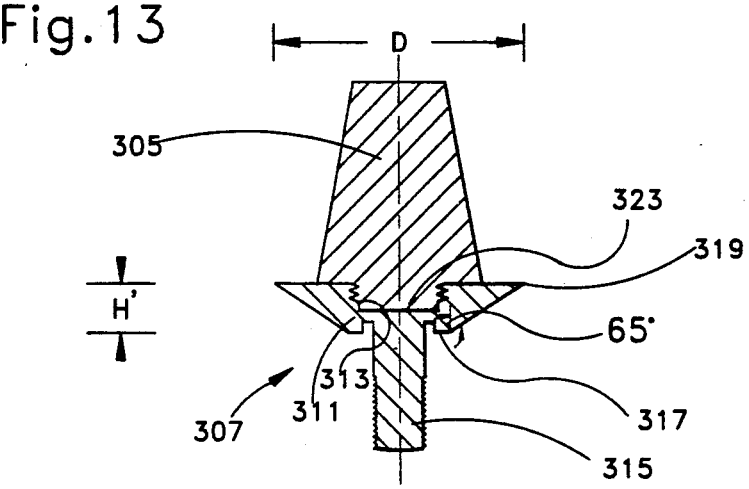
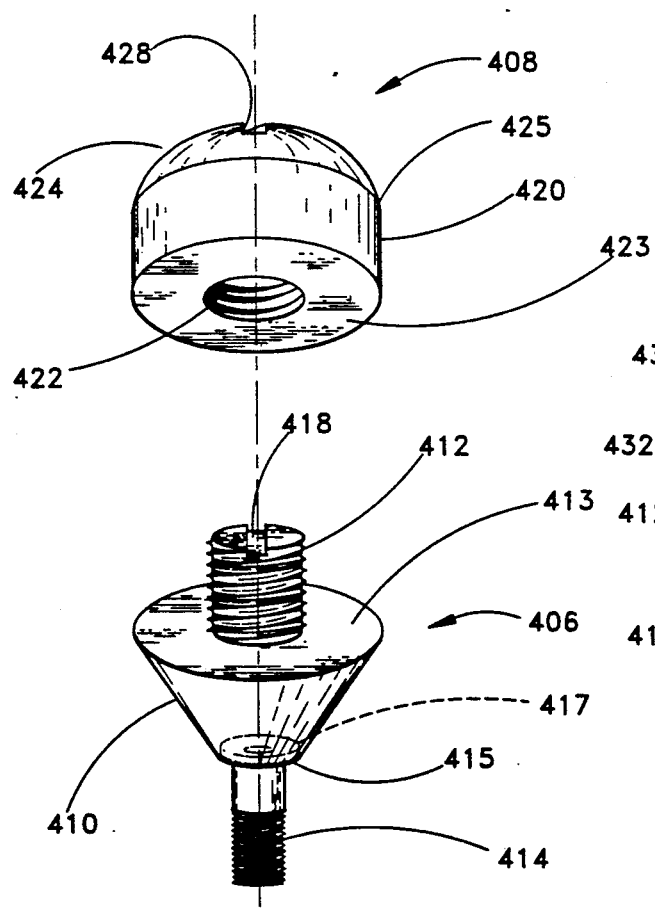
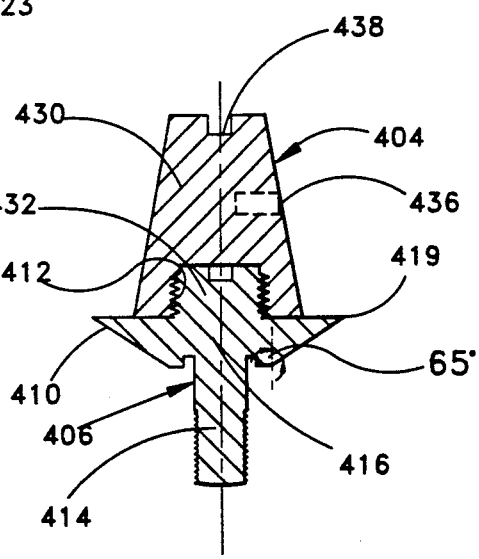

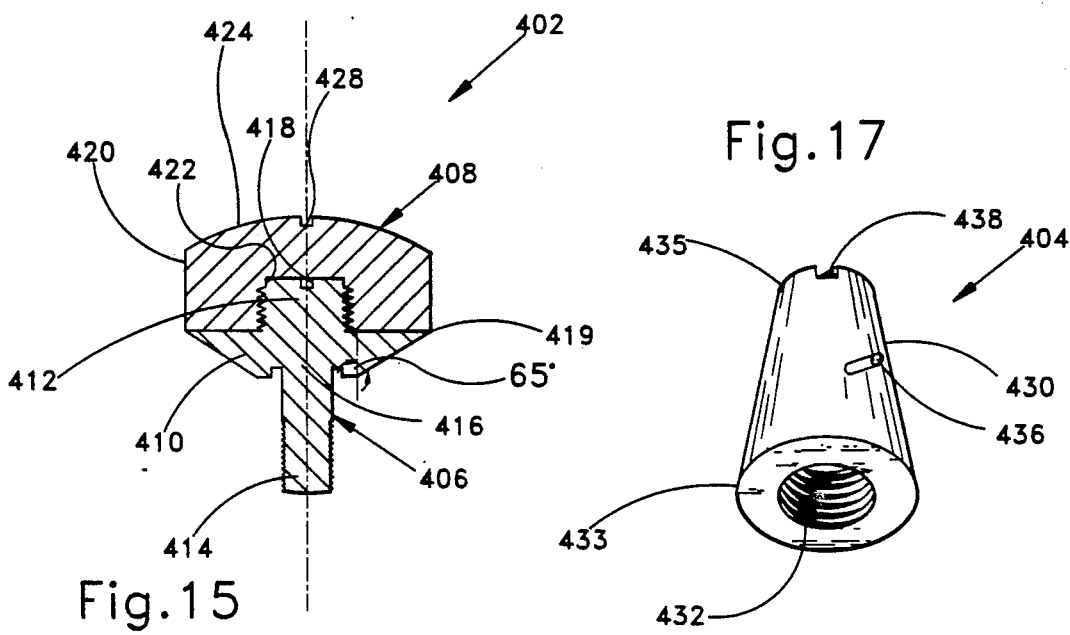
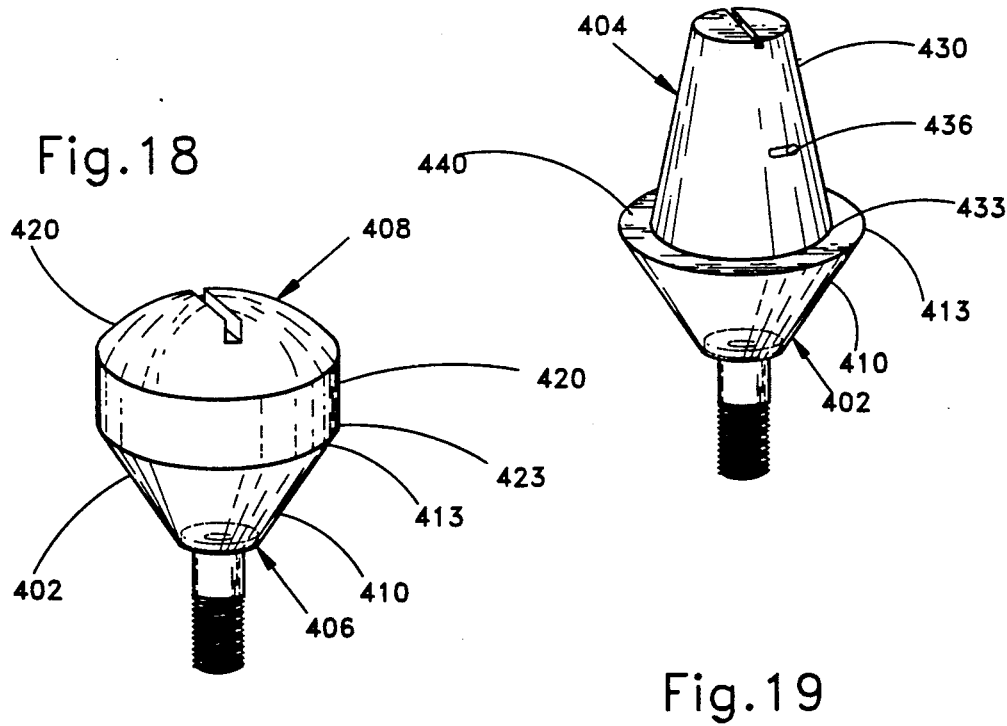

ANATOMICAL RESTORATION DENTAL IMPLANT SYSTEM WITH REINFORCED HEALING CAP AND ABUTMENT

This is a continuation-in-part of co-pending patent application Ser. No. 07/424,901, which was filed on Oct. 20, 1989, now U.S. Pat. No. 5,073,111.

BACKGROUND OF THE INVENTION

1. Field of the Invention

The present invention relates generally to the field of dental implants and in particular to a system providing a tooth analogue and a gingival tissue healing cap which results in a restoration having tissue-implant profiles similar to that of a natural tooth and its surrounding gingiva. The present invention also relates to fitting a tooth with a temporary crown and final prosthesis after the initial implant structure has been inserted and the surrounding tissue has healed. More particularly, the present invention relates to the field of anatomical restoration dental implant systems with reinforced healing cap and abutment.

2. Description of the Prior Art

Many systems have been proposed for rigidly fixing metal or ceramic materials to the alveolus of a human mandible or maxilla in an effort to provide a long term replacement for lost teeth. Early systems were successful for only limited periods of time and were eventually rejected as foreign bodies. Later systems, as described by U.S. Pat. Nos. 3,589,011 to Sneer, 3,797,113 to Brainin, 3,979,828 to Taylor, 4,324,550 to Reuther et al., and 4,416,679 to Mozsary et al., have proven to offer long term success by providing rigid anchorage in the support bone. Intraoral restoration of such ossointegrated devices has been accomplished with many different systems that modified the original attempts. Such modifications have been described in U.S. Pat. Nos. 4,780,080 to Harras, 4,713,003 to Symington et al., and 4,657,510 to Gittlemen. However, these restorative systems have required biologic and aesthetic compromises. The interface between an implant and its surrounding gingival tissue is often insufficiently close to prevent food and bacteria from entering this area. Such foreign matter can cause chronic infection and bone loss, resulting in eventual loss of the implant. Implants in current use have a round root form dimensionally different from that of a normal tooth root morphology. This makes aesthetic restoration difficult and impedes the development of a natural soft gingival tissue contour.

There exists a need for a dental implant system providing an implant root and gingival tissue interface having an improved resistance to bacterial infection and providing a contour more nearly approximating that of a natural tooth and its surrounding tissue.

In addition, since the fitting procedure of a temporary crown and then a permanent crown requires removal of the entire healing cap which causes damage to the surrounding tissue including apical migration of the tissue and in turn necessitates additional healing time, there is a further need for a dental implant system which permits a temporary crown and then a permanent crown to be fitted and implanted without disturbing the healed gingival tissues. There is also a need for a dental implant system which provides the best fitting with the gingival tissues with various angled and shaped healing caps and abutments.

The applicant is also the sole inventor of U.S. Pat. No. 5,035,619 (hereafter referred to as "the '619 patent"), which was issued on Jul. 30, 1991 from patent application Ser. No. 07/577,923 filed on Sep. 5, 1990, which in turn is also a continuation-in-part application of the original patent application Ser. No. 07/424,901. For the clarity of later discussion, hereafter patent application Ser. No. 07/424,901 will be referred to as "the original application," patent application Ser. No. 07/577,923 will be referred to as "the first continuation-in-part application," and this current application will be referred to as "the second continuation-in-part application."

Since it is more clear and logical to introduce first the present invention disclosed in the original application, the '619 patent will be discussed in detail thereafter.

SUMMARY OF THE INVENTION

The present invention is an anatomical restoration dental implant system with reinforced healing cap and abutment.

1. The Anatomical Restoration Dental Implant System

The present invention provides a system and a method for implanting tooth analogues in the alveolus of the jawbone. The emergence profile of the analogue more closely matches that of a natural root and the system provides a tight fit between the analogue and the gingiva upon installation of a crown or other tooth replacement.

The system comprises an implantable fixture having proximal and distal end portions, the proximal end portion having means for being implanted through opened gingival tissue into the alveolus of the jaw bone, the distal end portion being accessible from the outer surface of the jaw bone. The fixture contains a hollow interior beginning with an opening in the distal end portion and extending towards the proximal end portion. The hollow has threads along at least a portion of its length.

The invention utilizes a cover screw for sealing the hollow portion of the fixture during the time the jaw bone is growing about the fixture. After osseointegration of the fixture, the gingiva is reopened and the cover screw is removed and replaced by a healing cap. The healing cap provides a predetermined contour to the re-healing gingival tissue. The healing cap has a stem having proximal and distal end portions, a frusto-conical segment having larger and smaller ends, a cylindrical segment having proximal end distal ends, and a screwhead segment having a proximal end and a driven end. The proximal end portion of the stem is threaded within the hollow of the implantable fixture. The distal end portion of the stem is attached to the smaller end of the frusto-conical segment. The larger end of the frusto-conical segment is attached to the proximal end of the cylindrical segment. The distal end of the cylindrical segment is attached to the screwhead segment. The driven end of the screwhead segment is cooperable with a driving tool, such as a screwdriver. The axis of all the segments are in alignment with the axis of the stem.

After the re-opened gingival tissue has healed about the healing cap, the healing cap is removed and replaced with a hollow abutment having the same contour as that of the healing cap. Having the same contour permits the abutment to tightly fit the healed opening in the gingival tissue upon engagement of the abutment with the fixture. The abutment is removably affixed to the fixture by a screw having a threaded end portion and a driven end portion. The threaded end portion is passed through the abutment and threaded in the hollow of the fixture. The driven end portion of the screw is cooperable with a driving tool, such as a screwdriver and engages the abutment, holding the abutment in place against the fixture.

In a presently preferred embodiment, the abutment comprises a divergent segment and a head segment, the segments both having a frusto-conical shape. The smaller end of the divergent segment engages the distal end portion of the fixture, while the larger end of the divergent segment is attached to the smaller end of the head segment. Since the smaller end of the head segment is smaller than the larger end of the divergent segment, it creates a shoulder at their juncture. The axis of the divergent and head segments are in alignment with the axis of the fixture.

The system additionally comprises a tooth analogue releasibly engagable with the abutment. In a presently preferred embodiment, the analogue comprises a crown having a hollow interior adapted to fit on the head section of the abutment. The crown additionally has an opening extending laterally through the sidewall thereof. The opening is alignable with the threaded hollow in the side of the abutment. A holding screw secures the crown to the abutment. The screw has a threaded end portion and a driven end portion. The threaded end portion is passed through the opening in the side of the crown and is threaded in the opening in the side of the abutment. The driven end portion is cooperable with a driving tool and is engagable within a recess in the sidewall of the crown. With the exception of the crown, all elements of the invention are made of titanium or other rigid substance, compatible with implantation within the body.

To permit the abutment to tightly fit the healed opening in the gingival tissue upon engagement of the abutment with the fixture after the healing cap is removed, both the healing cap and the abutment have a similarly contoured frusto-conical or divergent segment. To provide the best fitting with the gingival tissues, the sidewall of the respective frusto-conical or divergent segment of the healing cap and the abutment is preferably extended outward from the smaller end of the segment at an angle alpha of between about 45 degrees and 65 degrees to the axis of the respective frusto-conical or divergent segment.

2. The Two-Part Healing Cap and Matching Abutment

In operation, the dental fixture remains in the jawbone and the healing cap is threaded into the fixture and held in place. The gingival tissues are then given time (usually at least eight weeks) to heal around the healing cap. The proper contouring of the gingival tissues during their healing is necessary to assure a tight fit between the abutment and the gingiva. During this time, osseointegration of the fixture to the jawbone also takes place. When it is time to test fit a crown, which initially is a temporary crown and subsequently a permanent crown, it is necessary to entirely remove the healing cap and replace it with the abutment.

By this time, the regrown gingival tissues have conformed to the shape of the frusto-conical segment of the healing cap. Therefore, when the healing cap is removed, at least some damage such as bruising and possibly some tissue removal is imparted to the regrown portion of gingival tissues adjacent the frusto-conical section. Furthermore, after the temporary crown is fitted, it is necessary to once again reinsert the healing cap and the gingival tissues must again be given time to regrow. Due to the bruising or tissue removal, the gingival tissues may not properly regrow in the manner originally formed against the frusto-conical section. This results in a delay of several additional weeks. In addition, this procedure must be repeated if it is necessary to refit the temporary crown and further must be repeated when it is time to fit the permanent crown.

To provide a desirable improvement, the present inventor previously invented a two-part healing cap and an abutment for use in conjunction with the two-part healing cap, instead of a one piece healing cap. The first part of the healing cap includes a divergent segment having the desired shape for the gingiva to heal around so that the gingival tissue heals in a contour reverse to the contour of the divergent segment. The second part of the healing cap includes a cylindrical portion having means which permits removable engagement with the first part of the healing cap at the adjoining end of the divergent segment of the first part of the healing cap, and a driven segment or screwhead in the second part of the healing cap joined to the cylindrical segment. During the healing, the second part of the healing cap can be removed from the first part of the healing cap, which in turn remains in the patient so that the healing of the gingiva is not disturbed. The abutment comprises a frusto-conical shaped head segment having means which permits removable engagement with the first part of the healing cap at the adjoining end of the divergent segment of the first part of the healing cap which remains in the patient. The tooth analogue is releasibly engagable with the abutment.

3. The Improved Two-Part Healing Cap and Matching Abutment

In the '619 patent issued from the first continuation-in-part application, the inventor conceived an improved two-part healing cap and an improved abutment for use in conjunction with the improved two-part healing cap. The first part of the improved healing cap includes a divergent or frusto-conical segment having the desired shape for the gingiva to heal around so that the gingival tissue heals in a contour reverse to the contour of the divergent segment. The second part of the improved healing cap includes a cylindrical portion having a threaded stem which permits removable engagement with the first part of the improved healing cap through a threaded hollow in the adjoining end of the divergent segment of the first part of the improved healing cap, and a driven segment or screwhead joined to the cylindrical segment. During the healing, the second part of the improved healing cap can be removed from the first part of the improved healing cap, which in turn remains in the patient so that the healing of the gingiva is not disturbed. The improved abutment comprises a frusto-conical shaped head segment with a threaded stem which permits removable engagement with the first of the improved healing cap through the threaded hollow in the adjoining end of the divergent segment of the first part of the improved healing cap which remains in the patient. The tooth analogue is releasibly engagable with the improved abutment.

The improved healing cap and abutment may be a preferred embodiment when the above-introduced angle alpha, which is the angle between the sidewall of the respective frusto-conical or divergent segment of the first part of the healing cap and the abutment and the axis of the respective segment, approaches the minimum end of the angle range that is about 45 degrees, for the reasons discussed later in detail.

4. The Reinforced Two-part Healing Cap and Matching Abutment

In this second continuation-in-part application, there is disclosed a reinforced two-part healing cap and a reinforced abutment for use in conjunction with the reinforced healing cap. The first part of the reinforced healing cap includes a divergent or frusto-conical segment having the desired shape for the gingiva to heal around so that the gingival tissue heals in a contour reverse to the contour of the divergent segment. The second part of the reinforced healing cap includes a cylindrical portion having a threaded hollow which permits removable engagement with the first part of the reinforced healing cap through a threaded stem in the adjoining end of the divergent segment of the first part of the reinforced healing cap, and a driven segment or screwhead joined to the cylindrical segment. During the healing, the second part of the reinforced healing cap can be removed from the first part of the reinforced healing cap, which in turn remains in the patient so that the healing of the gingiva is not disturbed. The reinforced abutment comprises a frusto-conical shaped head segment with a threaded hollow which permits removable engagement with the first part of the reinforced healing cap through the threaded stem in the adjoining end of the divergent segment of the first part of the reinforced healing cap which remains in the patient. The tooth analogue is releasibly engagable with the reinforced abutment.

The reinforced healing cap and abutment may be preferred when the above introduced angle alpha, which is the angle between the sidewall of the respective frusto-conical or divergent segment of first part of the healing cap and the abutment and the axis of the respective segment, is approaching the maximum end of the angle range that is about 65 degree, for the reasons discussed later in detail.

Further novel features and other objects of the present invention will become apparent from the following detailed description, discussion and the appended claims, taken in conjunction with the drawings.

BRIEF DESCRIPTION OF THE DRAWINGS

Referring particularly to the drawings for the purpose of illustration only and not limitation, there is illustrated:

FIG. 1 is a sectional view of a healing cap and fixture of a presently preferred embodiment of the invention showing a portion of the jawbone and gingiva in a broken away configuration.

FIG. 2 is a sectional view of a crown, abutment, fixture and holding screws of the presently preferred embodiment of the invention showing a portion of the jawbone and gingiva in a broken away configuration.

FIGS. 3-6 are side elevation views of preferred healing caps of the present invention.

FIG. 13 is a sectional view of a possible situation explored by the present invention regarding the application of the improved healing cap and improved abutment disclosed in the '619 patent.

FIG. 14 is a sectional view of a two part reinforced healing cap of the present invention, where the top part of the reinforced healing cap is screwed into the bottom part of the reinforced healing cap.

FIG. 15 is a sectional view of the reinforced abutment of the present invention screwed into the bottom part of a reinforced healing cap of the present invention, after the top part of the reinforced healing cap of the present invention has been removed.

FIG. 16 is a perspective view of the two-part reinforced healing cap of the present invention with the top part of the reinforced healing cap unscrewed from the bottom part of the reinforced healing cap.

FIG. 17 is a perpspective view of the reinforced abutment of the present invention.

FIG. 18 is a perspective view of the reinforced healing cap of the present invention with the two parts of the reinforced healing cap screwed together.

FIG. 19 is a perspective view the reinforced abutment screwed into the bottom part of the reinforced healing cap, after the top part of the reinforced healing cap has been removed, as disclosed by the present invention.

DESCRIPTION OF THE PREFERRED EMBODIMENT

Figure 6:
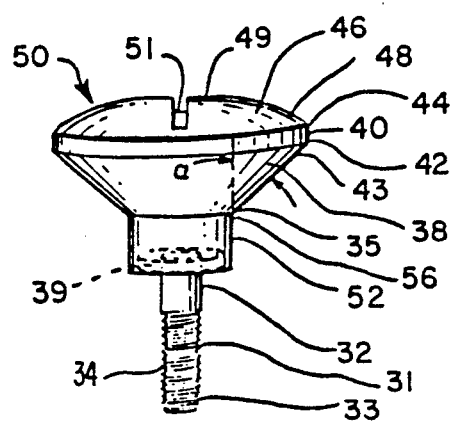

Although specific embodiments of the present invention will now be described with reference to the drawings, it should be understood that such embodiments are by way of example only and merely illustrative of but a small number of the many possible specific embodiments which can represent applications of the principles of the present invention. Various changes and modifications obvious to one skilled in the art to which the present invention pertains are deemed to be within the spirit, scope and contemplation of the present invention as further defined in the appended claims.

1. The Anatomical Restoration Dental Implant System

Referring now to FIGS. 1 and 2, the present invention is a method and a system of providing a tooth analogue for one or more missing teeth. The tooth analogue may comprise a crown, a fixed or removable partial denture, or a fixed or removable full denture. In a presently preferred embodiment of the invention the analogue comprises a crown 2 removably affixed to an abutment 4. According to the preferred method of installing the analogue in the mouth of a patient, a socket is prepared in the alveolus of the jawbone where a tooth has been extracted or otherwise lost. A conventional fixture 12 is implanted in this area. In one embodiment, the fixture is roughly cylindrical in shape and possesses a threaded surface 14. The fixture 12 includes a hollow portion 18 which extends from the upper surface 20 of the fixture toward the lower surface 22 thereof. The fixture is implanted such that the distal end portion 24 of the fixture extends to the outer surface of the jaw bone 26. The proxial end portion 28 of the fixture extends into the jaw bone 26 as far as is necessary for a satisfactory implantation. In one embodiment, the jawbone is drilled and threaded in preparation for receiving the fixture. During implantation, the threaded surface 14 of the fixture 12 threadably engages the threaded surface 29 of the jaw bone 26.

After implantation of the fixture 12, a cover is threaded into the fixture (not shown) to seal it during the period in which bone is growing about the proximal portion 28 of the fixture. The gingival tissue 37 above the fixture is closed according to procedures well known in the art. Upon completion of osseointegration of the fixture 12, the gingival tissue 37 above the fixture is reopened and the cover screw is removed. The healing cap 30 is then threaded into the fixture and held in place by stem 31. The stem has a distal end portion 32, and a proximal end portion 33, which together have a threaded surface 34. The threaded surface 34 is engaged with a threaded surface 36 within the hollow portion 18 of the fixture to hold the healing cap 30 in place. The fixture 12 has a raised lip 21 around the opening of the hollow 18 in the distal end portion 24 of the fixture. The lip 21 may be circular or hexagonal shape. The lip fits within appropriately configured socket 39 of the healing cap 30. The engagement of the lip within the socket provides additional support to the engagement of the healing cap 30 to the fixture 12.

The healing cap 30 is additionally configured to allow the gingival tissues 37, surgically displaced during removal of the cover screw to heal around the cap in a shape which is dimensionally similar to the tooth previously removed or lost. The proper contouring of the gingival tissues 37 during their healing is necessary to assure a tight fit between the abutment and the gingiva. This tight fit provides improved esthetics for the completed restoration.

Referring additionally now to FIGS. 3-6, preferred healing caps 30 may be configured in differing diameters, heights and emergence profiles to permit the gingival tissues 37 to be guided in healing to a proper form, commensurate with that desired at the completion of the restoration.

Details of three section healing caps 30 are shown in FIGS. 3 and 4. The caps have frusto-conical section 38, the smaller end 35 of which is attached to the distal end 32 of the stem 31. A cylindrical section 40 extends away from frusto-conical section 38, having a proximal end 42 attached to the larger end 43 of the frusto-conical section. A screwhead segment 46 terminates the healing cap 30, having a proximal end 48 which is attached to the distal end 44 of the cylindrical section 40. The screwhead segment 46 also has a driven end 49 cooperable with a driving tool. The driven end is preferably a slot 51 transverse to the long axis of the healing cap 30, which may be driven by a blade screwdriver.

Four section healing caps 50 are shown in FIGS. 5 and 6. These caps have the same elements as the three section caps 30 with the addition of a cylindrical shaped base 52. The base 52 is used to fill the space between the surface of the jaw bone and the distal portion 24 of the fixture 12 when the surface of the jaw bone, after healong about the fixture, extends above the distal portion of the fixture. The base 52 has a proximal end portion 54 and a distal end portion 55. The proximal end portion 54 is attached to the distal end portion 32 of the stem 31, and the distal end portion 55 is attached to the smaller end 35 of the frusto-conical section.

The long axes of the segments 38, 40, 46, 52 and the stem 31 of the healing caps 30, 50 are preferably aligned. At the juncture of the segments 52, 38, 40 and 46, the circumference of each segment is preferably the same as that of each adjoining segment.

After placement of the fixture 12 in the jaw bone 26 and a healing cap 30 or 50 through the gingival tissue 37, the gingiva is sutured about the cap. The fixture and cap are permitted to remain in place until a tooth analogue has been made and is ready for insertion into the fixture. This requires a period of eight weeks or longer. When the tooth analogue is ready for insertion the cap is removed from the fixture 12 and replaced with a tooth analogue including an abutment 4, 6, or 8.

Referring now to FIGS. 2 and 7-9, abutments 4, 6 and 8 are provided having different emergence profiles, in harmony with those of the healing caps 30, 50.

Figure 7:
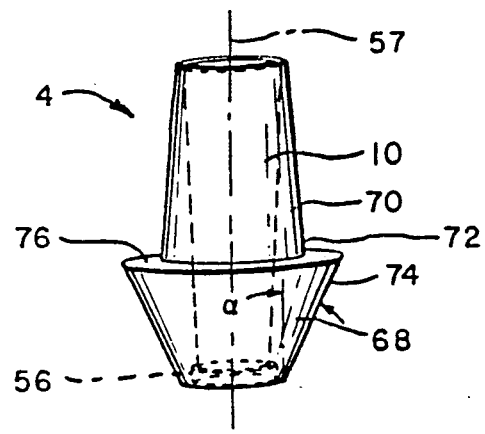
FIGS. 7-9 are side elevation views of preferred abutments of the present invention.
Figure 8:
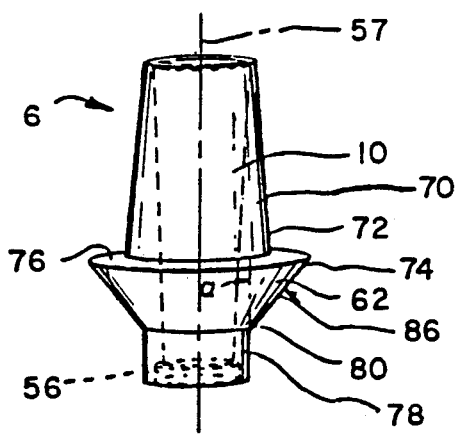
Figure 9:
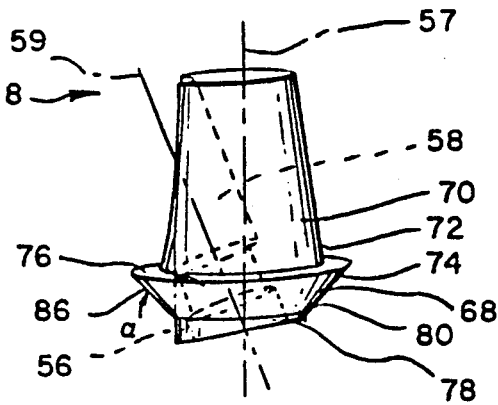

The abutment 4, 6, 8 has a socket 56 adapted to fit the lip 21 on the distal end portion 24 of the fixture 12. The engagement of the lip 21 and the socket 56 provides resistance to shear forces resulting from mastication. Referring to FIGS. 7 and 8, the abutments 4 and 6 have a hollow 10, extending from the socket 56, through the interior of the fixture, centered about the long axis 57 of the abutments 4 and 6. As shown in FIG. 9, a hollow 58 of the abutment 8 is symmetrical about an axis 59 offset from the long axis 57 of the abutment. The offset of the hollow 58 is selected to accommodate a malaligned implanted fixture, or to aid in paralleling abutments for fixed partial dentures. The hollow 58 may emerge partially or fully from the sidewall of the abutment.

Referring again to FIG. 2, the abutment 4 is secured to the fixture 12 by a screw 60 having a threaded end portion 61 and a driven end portion 62. The screw is passed through the abutment hollow 10 and engaged with the threaded surface 36 within the fixture 12. The driven end portion 62 of the screw 60 is preferably a slot 66, transverse to the long axis of the screw, which is cooperable with a blade screwdriver.

Referring now to FIGS. 7-9, the abutments 4, 6, and 8 are comprised of a divergent segment 68, and a head segment 70, both segments having a frusto-conical shape. The larger end 72 of the head segment 70 is affixed to and extends outward from the larger end 74 of the divergent segment 68. The larger end 74 of the divergent segment 68 is larger than the larger end 72 of the head segment 70 thereby creating a shoulder 76 at their juncture. This shoulder provides a surface through which chewing forces from the crown 2, or other tooth analogue, are transferred to the abutment 4, 6, 8.

The abutments 6 and 8 additionally comprise a cylindrically shaped base 78, as shown in FIGS. 8 and 9. The base is joined to and extends away from the smaller end 80 of the divergent segment 68. The end 82 of the base 78 is normal to the axis of the hollow 10, 58.

The long axes 57 of the abutments in FIGS. 7-9 are preferably in alignment, and the base 78 and the divergent segment 68 are preferably of the same circumference at their juncture. The abutments 4, 6, 8 are preferably made of a one piece construction. To provide the best fitting of the gingival tissues 37 with the abutment 4, 6, 8, the sidewall 84 of the frusto-conical segment of the healing cap 30, 50 and the sidewall 86 of the divergent segment 68 of the abutment, preferably extend outward from the smaller end of the segments at an angle alpha as shown in FIGS. 3, 7 and 8, of between 45 degrees and 65 degrees to the long axis of the segment.

A feature of the use of a screw 60 to secure the abutment 4, 6, 8 to the fixture 12 is that the divergent segment 68 can be prepared in the same manner as a natural tooth, with reduction of the occlusal, and proximal surfaces of the abutment as necessitated by the situation. Additionally, axial reduction of the abutment may be performed to facilitate fabricating anatomically correct restorations. Axial reduction also permits separation from adjacent teeth or implants, and varying cervical contours as required for tissue health and aesthetic appearance. Referring again to FIG. 2, the crown 2 is comprised of elements well known in the dental arts. The crown 2 has a hollow interior 88 adapted to fit on the head 70 of the abutment 4. The crown 2 may be releasibly attached to the abutment by a dental crown adhesive or by a screw. When the screw attachment method is used, a screw 90 is passed through an aperture 91 in the side of the crown. The abutment 4 has a threaded hollow 92 in its sidewall extending into the hollow 10 of the abutment. The screw 90 comprises a threaded end portion 94 and a driven end portion 96. The screw is passed through the aperture 91 and the threaded end portion 94 is engaged in the threaded hollow 92. The side of the crown additionally has a recess 98 which receives the driven end portion 96.

With the exception of the crown 2, all elements of the invention are preferably fabricated of pure titanium, but may be made of other biocompatable materials.

The dental implant system of the present invention provides for development of proper gingival tissue form resulting in more aesthetically and functionally desirable tissue contours at the time of and following tooth analogue connection. The system also allows modification and adaptation of the abutment 4, 6, 8 to meet intraoral demands in a manner similar to that used in the preparation and restoration of natural teeth. In view of the foregoing description of the invention in accordance with the requirements of the patent statutes, those skilled in the relevant arts will have no difficulties making changes and modifications in the different described elements of the invention in order to meet their specific requirements or conditions. For example, those elements having a driven end may comprise a socket cooperable with an allen wrench. Multiple as well as single restorations may be accomplished. Fixed full or partial dentures or removable prostheses may constitute the tooth analogues. Such changes and modifications may be made without departing from the scope and spirit of the present invention.

2. The Two-Part Healing Cap and Matching Abutment

In operation, the fixture 12 remains in the jawbone 26 and the healing cap 30 or 50 is threaded into the fixture and held in place by stem 31. As previously described, the threaded surface 34 of stem 31 is engaged with the threaded surface 36 within the hollow portion 18 of fixture 12 to hold the healing cap 30 or 50 in place. The gingival tissues 37 are then given time (usually at least eight weeks) to heel around the healing cap 30 or 50. The proper contouring of the gingival tissues 37 during their healing is necessary to assure a tight fit between the abutment and the gingiva. During this time, osseointegration of the fixture 12 to the jawbone 26 also takes place. When the dentist is ready to test fit a crown 2, which initially is a temporary crown and subsequently a permanent crown, it is necessary to entirely remove the healing cap 30 or 50 and replace it with the abutment 4, 6 or 8 in the manner previously described.

By this time, however, the regrown gingival tissues 37 have conformed to the shape of the frusto-conical section 38 of healing cap 30 or 50. Therefore, when the healing cap 30 or 50 is removed, at least some damage such as bruising and possibly some tissue removal is imparted to the regrown portion of gingival tissues 37 adjacent the frusto-conical section 38. Therefore, after the temporary crown is fitted, it is necessary to once again reinsert the healing cap 30 or 50 and the gingival tissues 37 must again be given time to regrow. Due to the bruising or tissue removal, the gingival tissues 37 may not properly regrow in the manner originally formed against the frusto-conical section 38. This results in a delay of several additional weeks. In addition, this procedure must be repeated if it is necessary to refit the temporary crown and further must be repeated when it is time to fit the permanent crown.

Therefore, an improvement is desirable wherein at least the frusto-conical portion 38 of healing cap 30 or 50 remains threaded into the jaw 26 and the frusto-conical portion 38 remains in its position within the regrown gingival tissues 37, thereby substantially reducing the trauma caused to the gingival tissues 37 when the temporary crown and later the permanent crown is fitted.

To provide a desirable improvement, the present inventor invented a two-part healing cap and an abutment for use in conjunction with the two-part healing cap, instead of a one piece healing cap. The first part of the healing cap includes a divergent segment having the desired shape for the gingiva to heal around so that the gingival tissue heals in a contour reverse to the contour of the divergent segment. The second part of the healing cap includes a cylindrical portion having means which permits removable engagement with the first part of the healing cap at the adjoining end of the divergent segment of the first part of the healing cap, and a driven segment or screwhead in the second part of the healing cap joined to the cylindrical segment.

During the healing process, the second part of the healing cap can be removed from the first part of the healing cap, which in turn remains in the patient so that the healing of the gingiva is not disturbed. The abutment comprises a frusto-conical shaped head segment having means which permits removable engagement with the first part of the healing cap at the adjoining end of the divergent segment of the first part of the healing cap which remains in the patient. The tooth analogue is releasibly engagable with the abutment.

3. The Improved Two-Part Healing Cap and Matching Abutment

Figure 10:
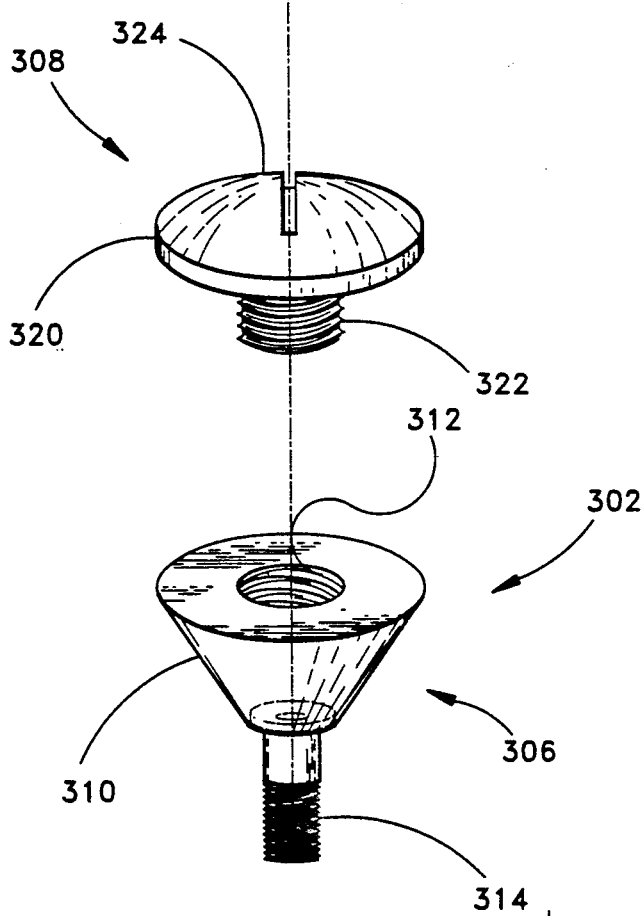
FIG. 10 is a perspective view of a two-part improved healing cap disclosed '619 patent issued to the present inventor, with the top part of the improved healing cap unscrewed from the bottom part of the improved healing cap.
Figure 11:
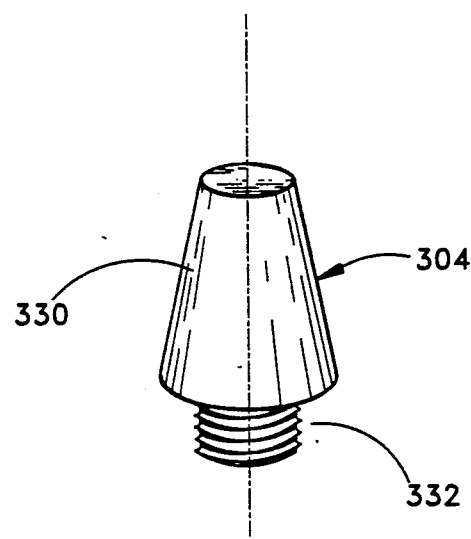
FIG. 11 is a perspective view of an improved abutment disclosed in the '619 patent issued to the present inventor.

In the '619 patent issued from the first continuation-in-part application, there was disclosed preferred embodiments of an improved two-part healing cap and an improved abutment for use in conjunction with the improved two-part healing cap. One of the perferred embodiments of the improved two-part healing cap 302 and the improved abutment 304 are shown in FIGS. 10 and 11 respectively. The improved healing cap 302 has a first part 306 and a second part 308. The first part 306 of the improved healing cap 302 includes a divergent or frusto-conical segment 310. The divergent segment 310 has the desired shape for the gingiva to heal around so that the gingival tissue heals in a contour reverse to the contour of the divergent segment 310. The divergent segment 310 also has a threaded hollow 312 recessed from its larger end and a stem 314 protruding from its smaller end. The second part 308 of the improved healing cap 302 includes a cylindrical portion 320 having a threaded stem 322 which permits removable engagement with the first part 306 of the improved healing cap 302 through the threaded hollow 312 of the divergent segment 310 of the first part 306 of the improved healing cap 302, and a driven segment or screwhead 324 joined to the cylindrical segment 320.

During the healing process, the second part 308 of the improved healing cap 302 can be removed from the first part 306 of the improved healing cap 302, which in turn remains in the patient so that the healing of the gingiva is not disturbed. The improved abutment 304 comprises a frusto-conical shaped head segment 330 with a threaded stem 332 which permits removable engagement with the first part 306 of the improved healing cap 302 through the threaded hollow 312 of the divergent segment 310 of the first part 306 of the improved healing cap 302 which remains in the patient. The tooth analogue is releasibly engagable with the improved abutment 304.

Figure 12:
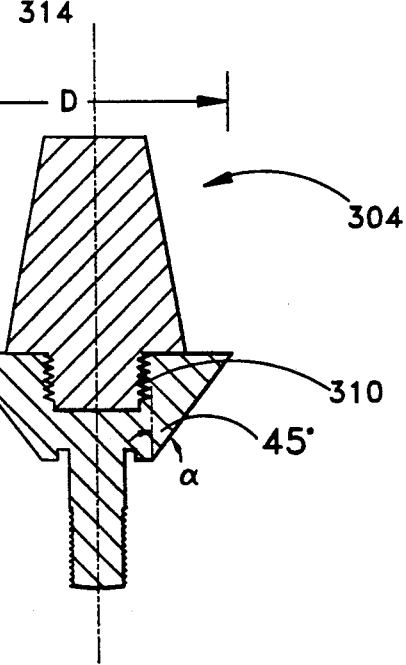
FIG. 12 is a sectional view of the improved abutment screwed into the bottom part of the improved healing cap, after the top part of the improved healing cap has been removed, as disclosed in the '619 patent.

Referring to FIG. 12, there is shown a sectional view of the improved abutment 304 screwed into the first part 306 of the improved healing cap 302, after the second part 308 of the improved healing cap 302 has been removed. It can be seen that once the diameter D of the large end of the divergent segment 310 is fixed, the thickness H of the divergent segment 310 is solely determined by the angle alpha between the axis and the sidewall of the divergent segment 310.

When the angle alpha is relatively large, for example close to 65 degrees, the thickness of the divergent segment of the first part of the healing cap is reduced. Referring to FIG. 13, there is shown a sectional view of an improved abutment 305 screwed into the first part 307 of an improved healing cap. The diameter D of the larger end of the divergent segment 311 of the first part 307 is equal to the one shown in FIG. 12, but the thickness H' of the divergent segment 311 is reduced to about only half of the thickness H of the divergent segment 310 shown in FIG. 12. This thinner divergent segment 311 presents several potential problems.

First, the threaded hollow 313 is shallower, which means that the length of the threaded stem 323 of the matching abutment 305 has to be reduced. This is undesirable because it reduces the bearing strength and stability of the abutment 305 which serves as the foundation of the tooth analogue.

Moreover, the layer 317 between the bottom of the threaded hollow 313 and the smaller end of the divergent segment 311 is thinner, which means that there is not very much material left in the divergent segment 311 for supporting the stem 315 of the first part 307 of this healing cap. This is also undesirable because it reduces the bearing strength and stability of first part 307 of this healing cap. Since the first part of the healing cap remains attached on the implant fixture to serve as the base of the abutment and the tooth analogue, its bearing strength and stability is very important to the overall implant system.

In addition, the circular edge 319 of the larger end of the divergent segment 311 becomes very sharp. To install the first part 307 of the healing cap onto the implant fixture, it needs to be rotated so the threaded stem 315 can be threaded into the threaded hollow of the implant fixture. It is very hard to rotate the first part 307 of the healing cap by holding the sharp circular edge 319. It is desirable if a driving tool such as a screwdriver could be used, especially when the first part 307 of the healing cap becomes so difficult to handle.

Since there are these potential problems presented when the angle alpha is relatively large, it may be preferable to utilize the improved healing cap and abutment disclosed in the '619 patent with the present invention dental implant system when the angle alpha is relatively small or approaching the minimum end of the angle range, which is about 45 degree. It may be preferable to utilize another type of healing cap and abutment which are reinforced when the angle alpha is relatively larger or approaching 65 degree, which thereby reduces the thickness of the divergent segment of the first part of the two-part healing cap.

4. The Reinforced Two-Part Healing Cap and Matching Abutment

To provide a desired solution to the potential problems presented earlier, which may arise from the reduced thickness of the divergent segment of the first part of the healing cap as the angle alpha between the axis and the sidewall of the divergent segment of the first part of the healing cap is increased. The present inventor in this second continuation-in-part application hereby discloses a reinforced two-part healing cap and a reinforced abutment for use in conjunction with the reinforced healing cap for the present invention anatomical restoration dental implant system.

Referring to FIGS. 14 and 15, there are shown a reinforced two-part healing cap 402 and reinforced abutment 404 of the present invention in respective combinations. Described generally, the reinforced healing cap 402 has a first part 406 and a second part 408. The first part 406 of the reinforced healing cap 402 includes a divergent or frusto-conical segment 410. The divergent segment 410 has the desired shape for the gingiva to heal around so that the gingival tissue heals in a contour reverse to the contour of the divergent segment 410. The divergent segment 410 of the reinforced healing cap 406 also has a threaded stem 414 protruding from its smaller end. The threaded stem can be threaded into the hollow of the dental implant fixture in the same manner as other healing caps described earlier.

However, in contrast to the divergent segment of the first part of the improved healing cap 306 or 307, the divergent segment 410 of the first part 406 of the reinforced healing cap 402 has a threaded stem 412 protruding from its larger end, to reinforce the central portion 416 of the first part 406 of the reinforced healing cap 402. The axis of the threaded stem 412 is aligned with the axis of the threaded stem 414. The structure of the first part 406 of the reinforced healing cap is much stronger because it is essentially an extended shank having a circular flange. This reinforced structure effectively increases the bearing strength and mounting stability of the first part 406 of the reinforced healing cap 402.

A groove or hex recess 418 may be provided at the top end of the threaded stem 412 of the first part 406 of the reinforced healing cap 402, so that when a dentist installs the first part 406 of the reinforced healing cap 402 onto the dental implant fixture, it can be rotated by using a screwdriver or an Allen Screw. This feature provides more effective threading of the first part 406 of the reinforced healing cap 402 without holding its sharp circular edge 419.

The matching second part 408 of the reinforced healing cap 402 includes a cylindrical portion 420 having a threaded hollow 422 which permits removable engagement with the first part 406 of the reinforced healing cap 402 through the threaded stem 412 of the divergent segment 410 of the first part 406 of the reinforced healing cap 402, and a driven segment or screwhead 424 joined to the cylindrical segment 420.

During the healing, the second part 408 of the reinforced healing cap 402 can be removed from the first part 406 of the reinforced healing cap 402, which in turn remains in the patient so that the healing of the gingiva is not disturbed. The reinforced abutment 404 comprises a frusto-conical shaped head segment 430 with a threaded hollow 432 which permits removable engagement with the first part 406 of the reinforced healing cap 402 through the threaded stem 412 of the first part 406 of the reinforced healing cap 402. Since the threaded stem 412 now has an adequate length, the attachment between the reinforced abutment 404 and the first part 406 of the reinforced healing cap 402 is strengthened.

A driven slot or hex recess 438 may also be provided at the top of the reinforced abutment 404, so that when a dentist installs the reinforced abutment 404 onto the first part 406 of the reinforced healing cap 402, it can be rotated by using a screwdriver or an Allen Screw. This feature provides an effective threading of the reinforced abutment 404.

The perspective views and detailed features of the reinforced healing cap 402 and mating abutment member 404 are illustrated in FIGS. 16 and 17 respectively. As with the healing caps illustrated in FIGS. 3–6, the reinforced healing cap 402 may be configured in differing diameters, heights and emergence profiles to permit the gingival tissues to be guided in healing to a proper form, commensurate with that desired at the completion of the restoration. In addition, although the reinforced healing cap 402 is illustrated as a three-segment healing cap comparable to the healing caps illustrated in FIGS. 3 and 4, it can also be composed in the form of four-segment healing caps illustrated in FIGS. 5 and 6 with the addition of a cylindrical shaped base section beneath the frusto-conical section.

Referring to FIG. 16, the first part 406 of the reinforced healing cap 402 has a divergent or frusto-conical segment 410, a threaded stem 412 which extends from the distal or larger end 413 of the divergent segment 410, and a threaded stem 414 which extends in the opposite direction from the proximal and smaller end 415 of the divergent segment 410. The threaded stem 412 and the threaded stem 414 are all axially aligned with the divergent segment 410. A driven slot or hex recess 418 is provided at the distal end of the threaded stem 412 of the first part 406 so it can be rotated by using a screwdriver or an Allen Screw. The divergent segment 410 also has a circular socket 417 at its proximal or smaller end 415, which is configured to permit raised lip 21 of dental implant fixture (See e.g. FIGS. 1 and 2) to fit within the socket 417, in the manner previously described. The lip 21 is circular in shape and the socket 417 is appropriately configured to the shape of the circular lip 21. The engagement of the lip 21 within the socket 417 provides additional support to the engagement of the first part 406 of the reinforced healing cap 402 to the dental implant fixture.

The second part 408 of the reinforced healing cap 402 has a cylindrical segment 420. The cylindrical segment 420 has a proximal end 423 and a distal end 425. A threaded hollow 422 is recessed from the proximal end 423 of the cylindrical segment. It matches with the threaded stem 412 at the distal end 413 of the divergent segment 410 of the first part 406. A screwhead or driven segment 424 is integrally formed from the distal end 425 of the cylindrical segment. The screwhead segment 424 terminates the healing cap 402. A driven slot or hex recess 428 is provided at the distal end of the screwhead segment 420 so it can be driven by a screwdriver or an Allen Screw. The threaded hollow 422 and the screwhead segment 424 are all axially aligned with the cylindrical segment 420.

The reinforced abutment 404 is illustrated in FIG. 17. The reinforced abutment 404 has a head segment 430 which is frusto-conical in shape. The larger or proximal end 433 of head segment 430 has a threaded hollow 432 recessed therefrom. It matches with the threaded stem 412 at the distal end 413 of the divergent segment 410 of the first part 406. A driven slot or hex recess 438 is provided at the top of the reinforced abutment 404 so it can be driven by using a screwdriver or an Allen Screw.

As shown in FIG. 18. when the first part 406 and the second part 408 of the reinforced healing cap 402 are threaded together, the proximal end 423 of the cylindrical segment 420 of the second part 408 contacts the distal or larger end 413 of the divergent segment 410 of the first part 406, and the first part 406 and the second part 408 of the reinforced healing cap 402 are axially aligned. In the preferred embodiment, the diameter of proximal end 423 of the cylindrical segment 420 is approximately equal to the diameter of the distal or large end 413 of divergent segment 410.

As shown in FIG. 19, when the reinforced abutment 404 and the first part 406 of the reinforced healing cap 402 are threaded together, the proximal end 433 of the head segment 430 of the reinforced abutment 404 contacts the distal or larger end 413 of the divergent segment 410 of the first part 406 of the healing cap 402, and the reinforced abutment 404 and the first part 406 of the reinforced healing cap 402 are axially aligned. In the preferred embodiment, the diameter of proximal end 433 of the reinforced abutment 404 is smaller than the diameter of the distal or large end 413 of divergent segment 410. Therefore, when the reinforced abutment 404 is screwed into the first part 406 of the healing cap 402, a shoulder 440 is created at their juncture.

The improvement in this design over the one piece healing cap 30 or 50 and one piece abutment 4, 6, 8, is apparent. The reinforcement in this design over the two-part healing cap 307 and matching abutment 305, where the angle alpha is relatively large, is also apparent. In operation, the first part 406 of reinforced healing cap 402 is threaded onto the dental implant fixture 12. As with the previous embodiment, the lip 21 of fixture 12 is accommodated into socket 417 at the proximal or smaller end 415 of the frusto-conical or divergent segment 410 of the first part 406 of the reinforced healing cap 402. The second part 408 of the reinforced healing cap 402 is threaded onto the first part 406. The gingival tissues 37 regrow as before and conform to the shape of the frusto-conical segment 410. At this time, after the gingival tissues 37 have regrown and it is necessary to replace the healing cap with an abutment, instead of having to remove the entire healing cap with the attendant potential for damage to regrown gingival tissue 37, the separate second part 408 of the reinforced healing cap 402 can be unscrewed from the first part 406 of the reinforced healing cap 402. The first part 406 remains at the distal end of the gingival tissues 37 and therefore very little if any of the regrown gingival tissues 37 are disturbed. After the second part 408 is unscrewed, the reinforced abutment 404 is screwed into the first part 406 of the reinforced healing cap 402. The threaded hollow 432 of the reinforced abutment 404 is threaded on stem 412 of the first part 406 of the reinforced healing cap 402, which eliminates the need for the long screw 60 of the previous embodiment. As a result, the shape of the reinforced abutment 130 screwed onto the first part 406 of the reinforced healing cap 402 is identical to the shape of the prior abutments 4, 6 or 8 but without the necessity of having to remove the first part 406 of the reinforced healing cap 402 and disturb the surrounding gingival tissues 37. In addition, since it is not necessary to unscrew threaded stem 414 of the first part 406 of the reinforced healing cap 402 from the fixture 12, their bond does not have to be broken. After the temporary crown has been fitted, it can be left in place on the reinforced abutment 404 and it is not necessary to replace them with the second part 408 of the reinforced healing cap 402, since no gingival tissues 37 have been disturbed and no regrowth time is required.

The crown is fitted over the reinforced abutment 404 in the same manner as it was fitted over head 70 of prior abutment embodiments, in the manner illustrated in FIG. 2. The crown 2 has a hollow interior 88 adapted to fit on the head segment 430 of the reinforced abutment 404. As with the previous embodiment, the crown 2 may be releasibly attached to the reinforced abutment 404 by a dental crown adhesive or by a screw. As with the embodiment illustrated in FIG. 2, when the screw attachment method is used, a screw 90 is passed through an aperture in the side of the crown. The head segment 430 of the reinforced abutment 404 may further have a threaded hollow 436 comparable to 92 in its sidewall extending into the head segment 430 of the reinforced abutment 404. The screw 90 comprises a threaded end portion 94 and a driven end portion 96. The screw is passed through the aperture 91 and the threaded end portion 94 is engaged in the threaded hollow 436. The side of the crown additionally has a recess 98 which receives the driven end portion 96.

In some applications, it may be necessary to use the healing caps which have a larger alpha angle, i.e., thinner divergent or frusto-conical segment, depending on the specific configuration of the jaw and tissues of the individual patient. In such a situation, the present invention reinforced healing cap and matching abutment is most advantageous. First, the structure of the first part 406 of the reinforced healing cap 402 is reinforced by eliminating the threaded hollow in the first part 406 of the reinforced healing cap 402, such as the hollow 313 of the prior healing cap 307 shown in FIG. 13. The first part 406 of the reinforced healing cap 402 is much stronger because it is almost an extended shank with a circular flange. This reinforced structure has significantly increased the bearing strength and mounting stability between the first part 406 of the reinforced healing cap 402 and the dental implant fixture 12. Second, the attachment between the reinforced abutment 404 and the first part 406 of the reinforced healing cap 402 is reinforced by having an adequately lengthened stem at the large end of the first part 406 of the reinforced healing cap 402. Again this reinforced structure has significantly increased the bearing strength and mounting stability between the first part 406 of the reinforced healing cap 402 and the reinforced abutment 404, which serves as the mounting base of the tooth analogue. In addition, all the components, including both the first part 406 and the second part 408 of the reinforced healing cap 402 and the reinforced abutment 404 can be driven and rotated by using driving tools.

It will be appreciated that, although the present invention reinforced healing cap and matching abutment is most advantageous for the situations where it is necessary to use healing caps having a larger alpha angle, the angle alpha of the divergent segment 410 of the first part 406 of the reinforced healing cap 402 is not limited to exactly or close to 65 degrees. As with the embodiments of the abutments illustrated in FIGS. 7-9, the angle alpha can vary between 65 degrees and 45 degrees, depending on the specific jaw and tissues condition of the individual patient.

The reinforced abutment 404 can also undergo axial reduction as with the prior abutment embodiments to facilitate fabricating anatomically correct restorations. As with prior abutment embodiments, axial reduction also permits separation from adjacent teeth or implants, and varying cervical contours as required for tissue health and aesthetic appearance. In addition, the first part 406 of the reinforced healing cap 402 may also have a cylindrical base segment integrally formed between the smaller or proximal end of the divergent or frusto-conical segment 410 and the threaded stem 414.

All components of the reinforced healing cap 402 and the matching abutment 404 are preferably made of titanium, but may also be made of other biocompatable materials.

Defined in detail, the present invention is a dental implant system implantable in the gingival tissue and the alveolus of the jaw bone comprising:

(a) an implantable fixture having proximal and distal end portions, the proximal end portion having means for being embedded in opened gingival tissue and the alveolus of the jaw bone, the distal end portion being accessible from the outer surface of the jaw bone, the fixture being made of a substance permitting healing of the opened gingival tissue and growth of the jaw bone about the fixture, the fixture further including a hollow extending from an opening in the distal end portion towards the proximal end portion, the hollow having threads along at least a portion of its length;

(b) means for sealing the hollow of the fixture during a period after implantation in which the jaw bone is growing about the proximal portion of the fixture;

(c) means for providing a predetermined contour to the gingival tissue adjacent the distal end of the fixture, such that the gingival tissue re-heals in a contour reverse to that of the contour of said means;

(d) a tooth analogue;

(e) reinforced abutment means for supporting the tooth analogue;

(f) means for releasibly attaching the tooth analogue to the reinforced abutment means;

(g) said contour means being a two part reinforced healing cap further comprising: (i) a first part including a proximal stem having proximal and distal end portions, the proximal portion of the proximal stem having threads which are threadable within the hollow of the implantable fixture, a frusto-conical segment, the smaller end of the segment being attached to the distal end of the proximal stem, with the axis of the segment being in alignment with the axis of the proximal stem, and a distal stem having proximal and distal ends and extending from the larger end of the frusto-conical segment, the axis of the distal stem aligned with the axis of the frusto-conical segment, the distal stem having a threaded surface; and (ii) a second part including a cylindrical segment having proximal and distal ends, the cylindrical segment further including a hollow extending from an opening in the proximal end of the segment towards the distal end of the segment, the hollow having threads along at least a portion of its length such that the distal stem of the first part is threadable within the hollow, and a screwhead segment having a proximal end and a driven end, the driven end cooperable with a driving tool, the proximal end being attached to the distal end of the cylindrical segment, with the axis of the screwhead segment being in alignment with the axis of the cylindrical segment; and (h) said reinforced abutment means further comprising a head segment having a frusto-conical shape, the head segment further including a hollow extending from an opening in the larger end of the segment towards the smaller end of the segment, the hollow having threads along at least a portion of its length such that the distal stem of the first part of the reinforced healing cap is threadable within the hollow;

(i) whereby the stem of said reinforced healing cap is threaded into the hollow of said fixture and the gingival tissue re-heals in a contour reverse to that of the contour of the frusto-conical portion of the reinforced healing cap, and thereafter the second part of the reinforced healing cap is unscrewed from the first part of the reinforced healing cap and the reinforced abutment means is screwed onto said first part of said reinforced healing cap and the tooth analogue is attached to the reinforced abutment means.

In one of the preferred embodiments of the present invention dental implant system defined in detail:

(a) the tooth analogue comprises a crown having a hollow interior adapted to fit on a portion of the reinforced abutment;

(b) the means for releasibly attaching the crown to the reinforced abutment further comprises: (i) a threaded hollow in the side of the reinforced abutment means; (ii) an opening extending laterally through the side of the crown, the crown opening alignable with the threaded hollow in the side of the reinforced abutment means; and (iii) a holding screw having a threaded end portion and a driven end portion, the threaded end portion passing through the opening in the side of the crown and threaded in the opening in the side of the reinforced abutment, the driven end portion cooperable with a driving tool and engagable with the crown;

(c) the means for releasibly attaching the tooth analogue to the reinforced abutment includes an adhesive;

(d) the reinforced healing cap additionally comprises a base, the base having a cylindrical shape with proximal and distal ends, the proximal end of the base being attached to the distal end portion of said proximal stem, and the distal end of the base being attached to the smaller end of said frusto-conical segment, with the axis of the base being in alignment with the axis of said proximal stem and said frusto-conical segment;

(e) regarding the reinforced healing cap, at the juncture between said screwhead segment and said cylindrical segment, the circumference of said screwhead segment is the same as the circumference of said cylindrical segment;

(f) regarding said reinforced healing cap, when the second part is screwed onto the first part, at the juncture between said cylindrical segment and said frusto-conical segment, the circumference of said cylindrical segment is the same as the circumference of said frusto-conical segment;

(g) the larger end of the frusto-conical segment of said reinforced healing cap is larger than the larger end of the head segment of said reinforced abutment means thereby creating a shoulder at their juncture;

(h) the distal stem of said first part of said reinforced healing cap further comprises at its distal end means cooperable with a driving tool; and (i) the head segment of said abutment means further comprises at its smaller end means cooperable with a driving tool.

Defined broadly, the present invention is a method for implanting a tooth in the gingival tissue and the alveolus of the jawbone comprising: (a) implanting a fixture having proximal and distal end portions, the proximal end portion having means for being embedded in opened gingival tissue and the alveolus of the jaw bone, the distal end portion being accessible from the outer surface of the jaw bone, the fixture being made of a substance permitting healing of the opened gingival tissue and growth of the jaw bone about the fixture, the fixture further including a hollow extending from the distal end portion toward the proximal end portion, the hollow being threaded along at least a portion of its length; (b) sealing the hollow of the fixture with a cover screw during a period after implantation in which the jaw bone is growing about the proximal portion of the fixture and the opened gingival tissue is healing, thereby preventing the jaw bone from entering the fixture; (c) reopening the gingival tissue and removing the cover screw, replacing the screw with a two part reinforced healing cap which includes a removable driven part and a frusto-conical part, the frusto-conical part having a stem threadable within a hollow on the frusto-conical part, the reinforced healing cap providing a predetermined contour to the gingival tissue adjacent the distal end of the fixture after the jaw bone has grown about the proximal portion of the fixture, thereby causing the gingival tissue to re-heal in a contour reverse to that of the frusto-conical portion of the reinforced healing cap provided; (d) removing the driven part of the reinforced healing cap and replacing it with reinforced abutment means having a hollow threadably engagable with the stem of the frusto-conical part of the reinforced healing cap, the reinforced abutment means used for supporting a tooth analogue with the implanted fixture; and (e) releasibly attaching a tooth analogue to the reinforced abutment means.

Defined alternatively, the present invention is a two part reinforced healing cap for use with an implantable fixture having an open end and a threaded hollow, the reinforced healing cap comprising:

(a) a first part further comprising: (i) a proximal stem having proximal and distal end portions, the proximal portion of the proximal stem having threads which are threadable within the hollow of the implantable fixture; (ii) a divergent segment, the smaller end of the segment being attached to the distal end of the proximal stem, with the axis of the segment being in alignment with the axis of the proximal stem; and (iii) a distal stem having proximal and distal ends and extending from the larger end of the divergent segment, the axis of the distal stem aligned with the axis of the divergent segment, the distal stem having a threaded surface; and (b) a second part further comprising: (i) a cylindrical segment having proximal and distal ends, the cylindrical segment further including a hollow extending from an opening in the proximal end of the segment towards the distal end of the segment, the hollow having threads along at least a portion of its length such that the distal stem of the first part is threadable within the hollow; and (ii) a screwhead segment having a proximal end and a driven end, the driven end cooperable with a driving tool, the proximal end being attached to the distal end of the cylindrical segment, with the axis of the screwhead segment being in alignment with the axis of the cylindrical segment.

Defined also alternatively, the present invention is a two part reinforced abutment device for use with an implantable fixture having an open end and a threaded hollow, the reinforced abutment device comprising:

(a) a first part further comprising: (i) a proximal stem having proximal and distal end portions, the proximal portion of the proximal stem having threads which are threadable within the hollow of the implantable fixture; (ii) a divergent segment, the smaller end of the segment being attached to the distal end of the proximal stem, with the axis of the segment being in alignment with the axis of the proximal stem; (iii) a distal stem having proximal and distal ends and extending from the larger end of the divergent segment, the axis of the distal stem aligned with the axis of the divergent segment, the distal stem having a threaded surface; and (b) the second part including a head segment having a frusto-conical shape, the head segment further including a hollow extending from an opening in the larger end of the segment towards the smaller end of the segment, the hollow having threads along at least a portion of its length such that the distal stem of the first part of the reinforced healing cap is threadable within the hollow.

Of course the present invention is not intended to be restricted to any particular form or arrangement, or any specific embodiment disclosed herein, or any specific use, since the same may be modified in various particulars or relations without departing from the spirit or scope of the claimed invention hereinabove shown and described of which the apparatus shown is intended only for illustration and for disclosure of an operative embodiment and not to show all of the various forms or modification in which the present invention might be embodied or operated.

The present invention has been described in considerable detail in order to comply with the patent laws by providing full public disclosure of at least one of its forms. However, such detailed description is not intended in any way to limit the broad features or principles of the present invention, or the scope of patent monopoly to be granted.

What is claimed is:

1. A dental implant system implantable in the gingival tissue and the alveolus of the jaw bone comprising:

a. an implantable fixture having proximal and distal end portions, the proximal end portion having means for being embedded in opened gingival tissue and the alveolus of the jaw bone, the distal end portion being accessible from the outer surface of the jaw bone, the fixture being made of a substance permitting healing of the opened gingival tissue and growth of the jaw bone about the fixture, the fixture further including a hollow extending from an opening in the distal end portion towards the proximal end portion, the hollow having threads along at least a portion of its length;

b. means for sealing the hollow of the fixture during a period after implantation in which the jaw bone is growing about the proximal portion of the fixture;

c. means for providing a predetermined contour to the gingival tissue adjacent the distal end of the fixture, such that the gingival tissue re-heals in a contour reverse to that of the contour of said means;

d. a tooth analogue;

e. reinforced abutment means for supporting the tooth analogue;

f. means for releasibly attaching the tooth analogue to the reinforced abutment means;

g. said contour means being a two part reinforced healing cap further comprising, (i) a first part including a proximal stem having proximal and distal end portions, the proximal portion of the proximal stem having threads which are threadable within the hollow of the implantable fixture, a frusto-conical segment, the smaller end of the segment being attached to the distal end of the proximal stem, with the axis of the segment being in alignment with the axis of the proximal stem, and a distal stem having proximal and distal ends and extending from the larger end of the frusto-conical segment, the axis of the distal stem aligned with the axis of the frusto-conical segment, the distal stem having a threaded surface, (ii) a second part including a cylindrical segment having proximal and distal ends, the cylindrical segment further including a hollow extending from an opening in the proximal end of the segment towards the distal end of the segment, the hollow having threads along at least a portion of its length such that the distal stem of the first part is threadable within the hollow, and a screwhead segment having a proximal end and a driven end, the driven end cooperable with a driving tool, the proximal end being attached to the distal end of the cylindrical segment, with the axis of the screwhead segment being in alignment with the axis of the cylindrical segment; and h. said reinforced abutment means further comprising a head segment having a frusto-conical shape, the head segment further including a hollow extending from an opening in the larger end of the segment towards the smaller end of the segment, the hollow having threads along at least a portion of its length such that the distal stem of the first part of the reinforced healing cap is threadable within the hollow;

i. whereby the stem of said reinforced healing cap is threaded into the hollow of said fixture and the gingival tissue re-heals in a contour reverse to that of the contour of the frusto-conical portion of the reinforced healing cap, and thereafter the second part of the reinforced healing cap is unscrewed from the first part of the reinforced healing cap and the reinforced abutment means is screwed onto said first part of said reinforced healing cap and the tooth analogue is attached to the reinforced abutment means.

2. The dental implant system of claim 1 wherein the tooth analogue comprises a crown having a hollow interior adapted to fit on a portion of the reinforced abutment.

3. The dental implant system of claim 2 wherein the means for releasibly attaching the crown to the reinforced abutment comprises:
a. a threaded hollow in the side of the reinforced abutment means;
b. an opening extending laterally through the side of the crown, the crown opening alignable with the threaded hollow in the side of the reinforced abutment means; and
c. a holding screw having a threaded end portion and a driven end portion, the threaded end portion passing through the opening in the side of the crown and threaded in the opening in the side of the reinforced abutment, the driven end portion cooperable with a driving tool and engagable with the crown.

4. The dental implant system of claim 1 wherein the means for releasibly attaching the tooth analogue to the reinforced abutment includes an adhesive.

5. The dental implant system of claim 1 wherein said reinforced healing cap additionally comprises a base, the base having a cylindrical shape with proximal and distal ends, the proximal end of the base being attached to the distal end portion of said proximal stem, and the distal end of the base being attached to the smaller end of said frusto-conical segment, with the axis of the base being in alignment with the axis of said proximal stem and said frusto-conical segment.

6. The dental implant system of claims 1 or 5 wherein regarding said reinforced healing cap, at the juncture between said screwhead segment and said cylindrical segment, the circumference of said screwhead segment is the same as the circumference of said cylindrical segment.

7. The dental implant system of claims 1 or 5 wherein regarding said reinforced healing cap, when the second part is screwed onto the first part, at the juncture between said cylindrical segment and said frusto-conical segment, the circumference of said cylindrical segment is the same as the circumference of said frusto-conical segment.

8. The dental implant system of claim 1 wherein the larger end of the frusto-conical segment of said reinforced healing cap is larger than the larger end of the head segment of said reinforced abutment means thereby creating a shoulder at their juncture.

9. The dental implant system of claims 1 or 5 wherein said distal stem of said first part of said reinforcecd healing cap further comprises at its distal end means cooperable with a driving tool.

10. The dental implant of claim 1 wherein said head segment of said abutment means further comprises at its smaller end means cooperable with a driving tool.

11. A two part reinforced healing cap for use with an implantable fixture having an open end and a threaded hollow, the reinforced healing cap comprising:
a. a first part further comprising,
(i) a proximal stem having proximal and distal end portions, the proximal portion of the proximal stem having threads which are threadable within the hollow of the implantable fixture;
(ii) a divergent segment, the smaller end of the segment being attached to the distal end of the proximal stem, with the axis of the segment being in alignment with the axis of the proximal stem;
(iii) a distal stem having proximal and distal ends and extending from the larger end of the divergent segment, the axis of the distal stem aligned with the axis of the divergent segment, the distal stem having a threaded surface; and
b. a second part further comprising,
(i) a cylindrical segment having proximal and distal ends, the cylindrical segment further including a hollow extending from an opening in the proximal end of the segment towards the distal end of the segment, the hollow having threads along at least a portion of its length such that the distal stem of the first part is threadable within the hollow; and
(ii) a screwhead segment having a proximal end and a driven end, the driven end cooperable with a driving tool, the proximal end being attached to the distal end of the cylindrical segment, with the axis of the screwhead segment being in alignment with the axis of the cylindrical segment.

12. The reinforced healing cap of claim 11 additionally comprising a base, the base having a cylindrical shape with proximal and distal ends, the proximal end of the base being attached to the distal end portion of the proximal stem, and the distal end of the base being attached to the proximal end of the divergent segment, with the axis of the base being in alignment with the axis of the proximal stem and the divergent segment.

13. The reinforced healing cap of claims 11 or 12 wherein, at the juncture of between said screwhead segment and said cylindrical segment, the circumference of said screwhead segment is the same as the circumference of said cylindrical segment.

14. The reinforced healing cap of claims 11 or 12 wherein, when the second part of the reinforced healing cap is screwed onto the first part of the reinforced healing cap, at the juncture between said cylindrical segment and said frusto-conical segment, the circumference of said cylindrical segment is the same as the circumference of said frusto-conical segment.

15. The reinforced healing cap of claims 11 or 12 wherein said distal stem of said first part of said reinforced healing cap further comprises at its distal end means cooperable with a driving tool.

16. A method for implanting a tooth in the gingival tissue and the alveolus of the jawbone comprising:
a. implanting a fixture having proximal and distal end portions, the proximal end portion having means for being embedded in opened gingival tissue and the alveolus of the jaw bone, the distal end portion being accessible from the outer surface of the jaw bone, the fixture being made of a substance permitting healing of the opened gingival tissue and growth of the jaw bone about the fixture, the fixture further including a hollow extending from the distal end portion toward the proximal end portion, the hollow being threaded along at least a portion of its length;
b. sealing the hollow of the fixture with a cover screw during a period after implantation in which the jaw bone is growing about the proximal portion of the fixture and the opened gingival tissue is healing, thereby preventing the jaw bone from entering the fixture;
c. reopening the gingival tissue and removing the cover screw, replacing the screw with a two part reinforced healing cap which includes a removable driven part and a frusto-conical part, the frusto-conical part having a stem threadable with a hollow on the removable driven part, the reinforced healing cap providing a predetermined contour to the gingival tissue adjacent the distal end of the fixture after the jaw bone has grown about the proximal portion of the fixture, thereby causing the gingival tissue to re-heal in a contour reverse to that of the frusto-conical portion of the reinforced healing cap provided;
d. removing the driven part of the reinforced healing cap and replacing it with reinforced abutment means having a hollow threadably engagable with the stem of the frusto-conical part of the reinforced healing cap, the reinforced abutment means used for supporting a tooth analogue with the implanted fixture; and
e. releasibly attaching a tooth analogue to the reinforced abutment means.

17. A two part reinforced abutment device for use with an implantable fixture having an open end and a threaded hollow, the reinforced abutment device comprising:
a. a first part further comprising,
(i) a proximal stem having proximal and distal end portions, the proximal portion of the proximal stem having threads which are threadable within the hollow of the implantable fixture;
(ii) a divergent segment, the smaller end of the segment being attached to the distal end of the proximal stem, with the axis of the segment being in alignment with the axis of the proximal stem;
(iii) a distal stem having proximal and distal ends and extending from the larger end of the divergent segment, the axis of the distal stem aligned with the axis of the divergent segment, the distal stem having a threaded surface; and
b. the second part including a head segment having a frusto-conical shape, the head segment further including a hollow extending from an opening in the larger end of the segment towards the smaller end of the segment, the hollow having threads along at least a portion of its length such that the distal stem of the first part of the reinforced abutment device is threadable within the hollow.

18. The reinforced abutment device of claim 17 wherein when the first part is screwed into the second part, the larger end of the divergent segment is larger than the larger end of the head segment thereby creating a shoulder at their juncture.

19. The dental implant system of claim 17 wherein said distal stem of said first part of said reinforced abutment device further comprises at its distal end means cooperable with a driving tool.

20. The dental implant system of claim 17 wherein said head segment of said abutment device further comprises at its smaller end means cooperable with a driving tool.

* * * * *